(12) United States Patent
Lee et al.

(10) Patent No.: US 11,786,450 B2
(45) Date of Patent: Oct. 17, 2023

(54) FUSION PROTEIN COMPRISING HEAT SHOCK PROTEIN 10 AND BRAZZEIN PROTEIN WITH ENHANCED ANTI-OXIDATION ACTIVITY AND SKIN CELL PROLIFERATION EFFECT AND ANTI-WRINKLE COSMETIC COMPOSITION COMPRISING THE SAME AS EFFECTIVE COMPONENT

(71) Applicants: NEXGEN BIOTECHNOLOGIES, INC., Seoul (KR); Sun Kyo Lee, Gyeonggi-do (KR)

(72) Inventors: Sun Kyo Lee, Gyeonggi-do (KR); Seong Ran Lee, Gyeonggi-do (KR); Han Bong Ryu, Seoul (KR); Tae Hyun Kim, Gyeonggi-do (KR); Tae Won Choi, Seoul (KR)

(73) Assignees: NEXGEN BIOTECHNOLOGIES, INC., Seoul (KR); Sun Kyo Lee, Gyeonggi-Do (KR)

( * ) Notice: Subject to any disclaimer, the term of this patent is extended or adjusted under 35 U.S.C. 154(b) by 1117 days.

(21) Appl. No.: 16/481,211

(22) PCT Filed: Jun. 1, 2017

(86) PCT No.: PCT/KR2017/005750
§ 371 (c)(1),
(2) Date: Jul. 26, 2019

(87) PCT Pub. No.: WO2018/216841
PCT Pub. Date: Nov. 29, 2018

(65) Prior Publication Data
US 2023/0190618 A1    Jun. 22, 2023

(30) Foreign Application Priority Data
May 26, 2017 (KR) .................. 10-2017-0065255

(51) Int. Cl.
| | |
|---|---|
| *A61K 8/64* | (2006.01) |
| *A61Q 19/08* | (2006.01) |
| *C07K 14/245* | (2006.01) |
| *C07K 14/425* | (2006.01) |
| *C12N 15/70* | (2006.01) |

(52) U.S. Cl.
CPC .............. *A61K 8/645* (2013.01); *A61Q 19/08* (2013.01); *C07K 14/245* (2013.01); *C07K 14/425* (2013.01); *C12N 15/70* (2013.01); *C07K 2319/00* (2013.01); *C12N 2800/101* (2013.01); *C12N 2800/22* (2013.01)

(58) Field of Classification Search
CPC ...... A61K 8/645; A61Q 19/08; C07K 14/245; C07K 14/425; C07K 2319/00; C12N 15/70; C12N 2800/101
See application file for complete search history.

(56) References Cited

U.S. PATENT DOCUMENTS

2011/0243921 A1* 10/2011 Anders ................... A61P 17/00
424/649

FOREIGN PATENT DOCUMENTS

| | | |
|---|---|---|
| KR | 10-2012-0090019 B1 | 8/2012 |
| KR | 10-2016-0084825 A | 7/2016 |
| KR | 10-1636846 B1 | 7/2016 |
| KR | 10-1652956 B1 | 8/2016 |
| KR | 10-1678392 B1 | 11/2016 |
| WO | WO 2013/148258 A1 | 10/2013 |
| WO | WO 2016/077457 A1 | 5/2016 |

OTHER PUBLICATIONS

International Search Report for PCT/KR2017/005750 dated Feb. 19, 2018.
Douglas Hanahan, "Studies on Transformation of *Escherichia coli* with Plasmids", J. Mol. Biol. vol. 166, pp. 657-580, 1983.

* cited by examiner

*Primary Examiner* — Li N Komatsu
(74) *Attorney, Agent, or Firm* — The PL Law Group, PLLC

(57) ABSTRACT

A fusion protein includes heat shock protein 10 and brazzein protein. The fusion protein has an enhanced anti-oxidation activity and skin cell proliferation effect. It can be used as a cosmetic composition for ameliorating skin wrinkles. The cosmetic composition including the fusion protein can be advantageously used in future as a material of a functional cosmetic product.

13 Claims, 4 Drawing Sheets
Specification includes a Sequence Listing.

FUSION PROTEIN COMPRISING HEAT SHOCK PROTEIN 10 AND BRAZZEIN PROTEIN WITH ENHANCED ANTI-OXIDATION ACTIVITY AND SKIN CELL PROLIFERATION EFFECT AND ANTI-WRINKLE COSMETIC COMPOSITION COMPRISING THE SAME AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/005750, filed Jun. 1, 2017, which claims priority to the benefit of Korean Patent Application No. 10-2017-0065255 filed in the Korean Intellectual Property Office on May 26, 2017, the entire contents of which are incorporated herein by reference.

A sequence listing electronically submitted with the present application on Jul. 26, 2019 as an ASCII text file named 20190726_Q13319GR07_TU_SEQ, created on Jul. 19, 2019 and having a size of 7000 bytes, is incorporated herein by reference in its entirety.

TECHNICAL FIELD

The present invention relates to a fusion protein comprising heat shock protein 10 and brazzein protein with enhanced anti-oxidation activity and skin cell proliferation effect, and an anti-wrinkle cosmetic composition containing the fusion protein as an effective component.

BACKGROUND ART

Heat shock protein is one of the proteins that are expressed in cells in response to exposure to an extreme environment to prevent damages occurring in cell. Most of the heat shock proteins have a chaperon function for preventing functional loss of a protein that is caused by exposure to an extreme environment, and a great amount of energy (i.e., ATP) is required for the process. In skin, high temperature and ultraviolet ray are representative examples of the extreme environment, and, in particular, ultraviolet ray is the direct cause of skin aging. In recent years, studies are made on a heat shock protein which exhibits an ultraviolet ray-shielding effect, and various attempts are also made to use a heat shock protein as a component of a cosmetic composition.

Brazzein is a sweet-tasting protein which has been extracted first from the West African fruit of *Pentadiplandra brazzeana* Baillon. Compared to sucrose, brazzein shows sweetness that is about 500 to 2,000 times stronger than sucrose, and the major type of brazzein extracted from plants has 54 amino acids including pyroglutarmic acid residue at the amino terminal. On the other hand, the minor type of brazzein has only 53 amino acid residues without having pyroglutarmic acid at the amino terminal, and it shows sweetness that is about 2 times stronger than the major type brazzein. With molecular weight of about 6.5 kDa, brazzein has the smallest size among sweet-tasting proteins, and it is a monomer consisting of one subunit. Specifically, brazzein consists of one α-helix and two strands of β-sheet. By having 8 cysteine residues, brazzein forms four disulfide bonds in the molecule, and thus it has very high heat stability. Brazzein is also characterized in that it has very high solubility in water and very high pH stability.

In the present invention, a fusion protein having excellent skin regeneration effect is developed according to fusion between heat shot protein 10 and brazzein protein, and a cosmetic composition for skin regeneration and wrinkle improvement which contains the fusion protein as an effective component is developed.

Meanwhile, in Korean Patent Application Publication No. 2016-0084825, "Composition for preventing and alleviating ultraviolet-induced skin hypersensitivity" which comprises an extract of onion skin for suppressing expression of Hsp70 is disclosed, and in Korean Patent Registration No. 1239669, "Recombinant expression vector for brazzein expression and method for mass production of brazzein using the same" is disclosed. However, the fusion protein comprising heat shock protein 10 and brazzein protein with enhanced anti-oxidation activity and skin cell proliferation effect, and an anti-wrinkle cosmetic composition containing the fusion protein as an effective component as described in the present invention are not disclosed before.

SUMMARY

The present invention is devised under the circumstances described above, and the inventors of the present invention prepared a novel fusion protein according to fusion between a gene encoding the heat shock protein 10 and a gene encoding the brazzein protein, in which the genes are *E. coli* codon-optimized. It was found that the fusion protein prepared by the fusion between the heat shock protein 10 and brazzein protein has a more excellent anti-oxidation effect than the individual proteins, and, as a result of treating skin cell line with the fusion protein, a more excellent cell proliferation effect is obtained from a treatment with the fusion protein compared to a treatment with the individual proteins, and the present invention is completed accordingly.

To solve the problems described in the above, the present invention provides a fusion protein comprising heat shock protein 10 and brazzein protein with enhanced anti-oxidation activity and skin cell proliferation effect in which the fusion protein consists of the amino acid sequence of SEQ ID NO: 2 or SEQ ID NO: 4.

The present invention further provides a gene encoding the fusion protein.

The present invention further provides a recombinant vector comprising the aforementioned gene.

The present invention further provides a host cell transformed with the aforementioned recombinant vector.

The present invention further provides a method for producing in a host cell a fusion protein comprising heat shock protein 10 and brazzein protein including transforming a host cell with the aforementioned recombinant vector.

The present invention further provides a fusion protein comprising heat shock protein 10 and brazzein protein produced by the aforementioned method.

The present invention still further provides an anti-wrinkle cosmetic composition containing, as an effective component, a fusion protein comprising heat shock protein 10 and brazzein protein which consists of the amino acid sequence of SEQ ID NO: 2 or SEQ ID NO: 4.

The production method of the present invention in which the production in *Escherichia coli* (*E. coli*) is made by using a gene encoding the heat shock protein 10 and a gene encoding the brazzein protein, in which the genes are *E. coli* codon-optimized, enables a simplified production process because the recombinant fusion protein is expressed in form of an inclusion body in *E. coli*, and it also enables production of the recombinant protein in large amount. Furthermore, the fusion protein comprising heat shock protein 10 and brazzein protein which is produced by the aforementioned method has an excellent anti-oxidation activity and an excellent skin regeneration effect, and thus it is expected that the fusion protein can be advantageously used as a raw material of a novel functional cosmetic for skin whitening or amelioration of skin wrinkles.

DETAILED DESCRIPTION

Figure 1:
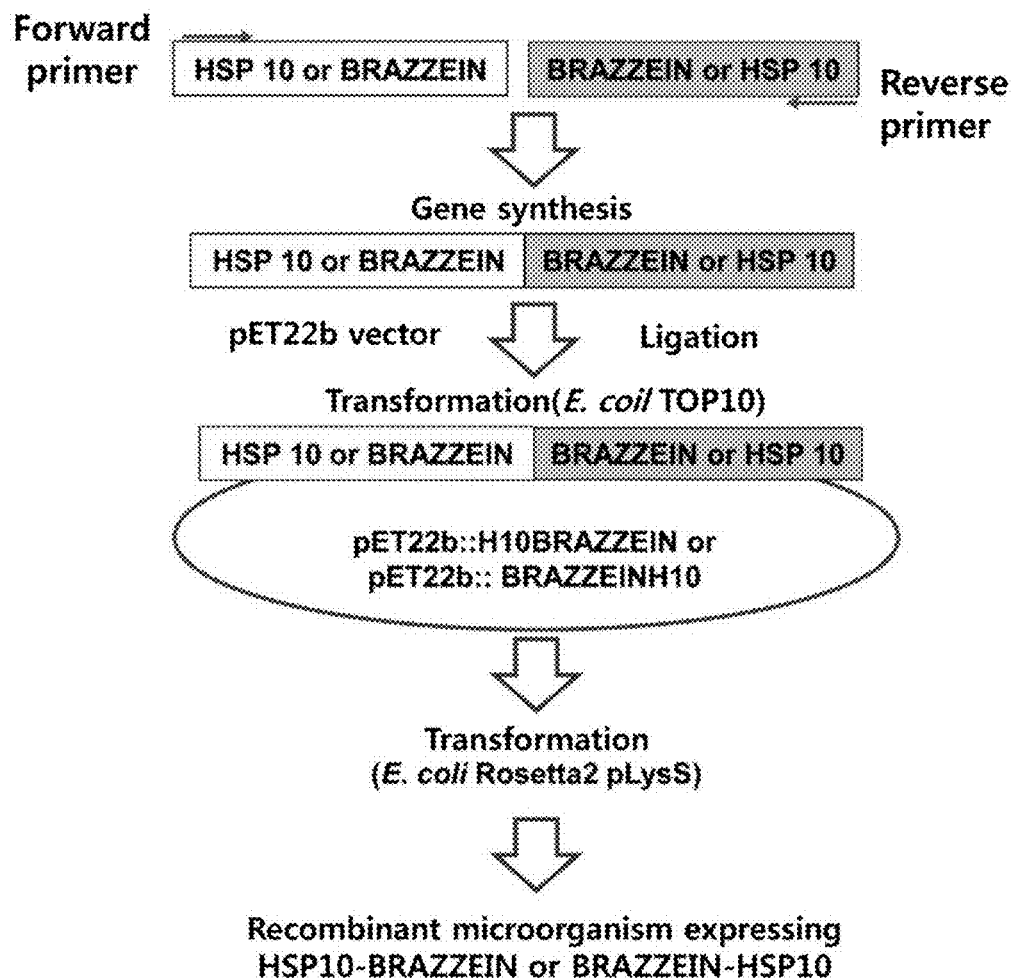
FIG. 1 is a schematic drawing illustrating the process of producing the recombinant plasmid (pET22b::H10BRAZZEIN and pET22b::BRAZZEINH10) which contains a gene encoding the fusion protein of heat shock protein 10 (HSP10) and brazzein protein, and transformation of E. coli with the recombinant plasmid.

To achieve the aforementioned object of the present invention, the present invention provides a fusion protein comprising heat shock protein 10 and brazzein protein with enhanced anti-oxidation activity and skin cell proliferation effect in which the fusion protein consists of the amino acid sequence of SEQ ID NO: 2 or SEQ ID NO: 4.

A protein having the amino acid sequence represented by SEQ ID NO: 2 (i.e., brazzein protein is fused to the amino terminal of heat shock protein 10; BRAZZEIN-HSP10) or SEQ ID NO: 4 (i.e., brazzein protein is fused to the carboxy terminal of heat shock protein 10; HSP10-BRAZZEIN), and also functional equivalents of the protein fall within the scope of the fusion protein comprising heat shock protein 10 and brazzein protein of the present invention. The term "functional equivalents" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2 or SEQ ID NO: 4, and it indicates a protein exhibiting substantially the same activity as the protein represented by SEQ ID NO: 2 or SEQ ID NO: 4. The expression "substantially the same activity" means an anti-oxidation effect and a cell regeneration effect. Also included in the present invention are fragments, derivatives, and analogues of the fusion protein comprising heat shock protein 10 and brazzein protein. The terms "fragments", "derivatives", and "analogues" that are described in the present specification indicate a polypeptide with the substantially same biological function or activity as the fusion protein comprising heat shock protein 10 and brazzein protein of the present invention.

The fusion protein comprising heat shock protein 10 and brazzein protein of the present invention preferably consists of the amino acid sequence of SEQ ID NO: 2 or SEQ ID NO: 4, in which the fusion protein consisting of the amino acid sequence of SEQ ID NO: 2 is a novel protein that is produced by fusion between the brazzein protein consisting of the $1^{st}$ to the $55^{th}$ amino acids and the heat shock protein 10 consisting of the $56^{th}$ to the $157^{th}$ amino acids of SEQ ID NO: 2 while the fusion protein consisting of the amino acid sequence of SEQ ID NO: 4 is a novel protein that is produced by fusion between the heat shock protein 10 consisting of the $1^{st}$ to the $102^{nd}$ amino acids and the brazzein protein consisting of the $103^{rd}$ to the $157^{th}$ amino acids of SEQ ID NO: 4.

The present invention further provides a gene encoding the fusion protein comprising heat shock protein 10 and brazzein protein which has an enhanced anti-oxidation activity and skin cell regeneration effect. The gene may consist of the E. coli codon-optimized nucleotide sequence of SEQ ID NO: 1 or SEQ ID NO: 3, but it is not limited thereto.

This gene encoding the fusion protein comprising heat shock protein 10 and brazzein protein with enhanced anti-oxidation activity and skin cell regeneration effect of the present invention may include the nucleotide sequence of SEQ ID NO: 1 (i.e., gene encoding a protein in which brazzein protein is fused to the amino terminal of heat shock protein 10) or SEQ ID NO: 3 (i.e., gene encoding a protein in which brazzein protein is fused to the carboxy terminal of heat shock protein 10). Furthermore, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence selected from a group consisting of SEQ ID NO: 1 and SEQ ID NO: 3. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

"Codon-optimized" means a modification of codon of a polynucleotide encoding a protein with a codon that is used first than others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism. The nucleotide sequence of SEQ ID NO: 1 or SEQ ID NO: 3 of the present invention is a sequence which has been optimized to E. coli codon such that the gene encoding the fusion protein comprising heat shock protein 10 and brazzein protein can be expressed in E. coli.

The present invention further provides a recombinant vector comprising the aforementioned gene, and a host cell transformed with the recombinant vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding a fusion protein comprising heat shock protein 10 and brazzein protein can be inserted to a recombinant expression vector. The term "recombinant expression vector" means bacteria plasmid, phage, yeast plasmid, plant cell virus, mammalian cell virus, or other vector. In general, any plasmid and vector can be used if it can replicate and is stabilized in a host. Important characteristics of the expression vector include that it comprises a replication origin, a promoter, a marker gene, and a translation control element.

The expression vector comprising the gene sequence encoding a fusion protein comprising heat shock protein 10 and brazzein protein and an appropriate signal for regulating transcription/translation can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

The recombinant vector according to one embodiment of the present invention is prepared by in-frame fusion of 5' terminal (NdeI restriction enzyme site) and 3' terminal (XhoI restriction enzyme site) of a synthesized gene encoding the fusion protein comprising heat shock protein 10 and brazzein protein (i.e., SEQ ID NO: 1 or SEQ ID NO: 3) to pET22b vector, and it may be a recombinant vector characterized in that it can produce the fusion protein comprising heat shock protein 10 and brazzein protein based on effective expression of the aforementioned gene with an aid of lac promoter (lac promoter) and lacI repressor (lacI repressor), but it is not limited thereto.

For a host cell having an ability of having stable and continuous cloning and expression of the vector of the present invention in a prokaryotic cell, any host cell known in the pertinent art can be used. Examples of the prokaryotic cells include, *Bacillus* sp. strain including *E. coli* Rosetta, *E. coli* JM109, *E. coli* BL21, *E. coli* RR1, *E. coli* LE392, *E. coli* B, *E. coli* X 1776, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

Furthermore, when an eukaryotic cell is transformed with the vector of the present invention, yeast (*Saccharomyce cerevisiae*), an insect cell, a human cell (for example, CHO (Chinese hamster ovary) cell line, W138, BHK, COS-7, HEK 293, HepG2, 3T3, RIN, and MDCK cell line), a plant cell, and the like can be used as a host cell.

The transformed host cell of the present invention may be *E. coli* Rosetta2 (DE3) pLysS cell line, but it is not limited thereto.

When a host cell is a prokaryotic cell, delivery of the vector of the present invention into a host cell can be carried out by $CaCl_2$ method, Hanahan's method (Hanahan, D., *J. Mol. Biol.,* 166:557-580 (1983)) or an electroporation method, and the like. In addition, when a host cell is an eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method for producing in a host cell a fusion protein comprising heat shock protein 10 and brazzein protein including transforming a host cell with the aforementioned recombinant vector to overexpress a gene encoding a fusion protein comprising heat shock protein 10 and brazzein protein, and also a fusion protein comprising heat shock protein 10 and brazzein protein produced by the aforementioned method.

In the method according to one embodiment of the present invention, the host cell may be preferably *E. coli*, and more preferably *E. coli* Rosetta2 (DE3) pLysS cell line, but it is not limited thereto.

The present invention still further provides an anti-wrinkle cosmetic composition containing, as an effective component, a fusion protein comprising heat shock protein 10 and brazzein protein which consists of the amino acid sequence of SEQ ID NO: 2 or SEQ ID NO: 4.

In the cosmetic composition according to one embodiment of the present invention, content of the fusion protein comprising heat shock protein 10 and brazzein protein may be 0.000001 to 0.00002% by weight relative to the total weight of the cosmetic composition, but it is not limited thereto.

In the cosmetic composition of the present invention, components that are typically used for a cosmetic composition are included in addition to the effective component described above. Examples thereof include a lipid material, an organic solvent, a dissolution agent, a condensation agent, a gelling agent, a softening agent, an anti-oxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or liphophilic activating agent, a common auxiliary agent such as lipid vesicle, and a carrier.

The composition of the present invention can be prepared in any formulation which is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but not limited thereto. More specifically, the composition may be formulated into a skin, a skin softener, a skin toner, an astringent, a lotion, a milk lotion, a moisture lotion, a nutrition lotion, a massage crème, a nutrition crème, an eye crème, a moisture crème, a hand crème, an essence, a nutrition essence, a pack, a cleansing foam, a cleansing water, a cleansing lotion, a cleansing crème, a body lotion, a body cleanser, a soap, a powder, or the like.

In a case in which the cosmetic composition of the present invention has a formulation type of paste, crème, or gel, it is possible to use, as a carrier component, animal oil, plant oil, wax, paraffin, starch, tragacanth, cellulose derivatives, polyethylene glycol, silicone, bentonite, silica, talc, or zinc oxide.

In a case in which the cosmetic composition of the present invention has a formulation type of powder or spray, it is possible to use, as a carrier component, lactose, talc, silica, aluminum hydroxide, calcium silicate, or polyamide powder, when it is spray, in particular, a propellant such as chlorofluoro hydrocarbon, propane/butane, or dimethyl ether may be additionally contained.

In a case in which the cosmetic composition of the present invention has a formulation type of solution or emulsion, a solvent, a dissolution agent, or an emulsifier is used as a carrier component, and examples thereof include water, ethanol, isopropyl alcohol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethlyene sorbitol ester, or polyoxyethylene sorbitan ester, microcrystalline cellulose, aluminum metahydroxide, bentonite, agar, or tragacanth.

Hereinbelow, the present invention is explained in greater detail in view of the Examples. However, it is evident that the following Examples are given only for exemplification of the present invention and by no means the present invention is limited to the following Examples.

EXAMPLES

Example 1. Preparation of Recombinant Expression Vector and Transformed Recombinant Microorganism for Producing Fusion Protein Comprising Heat Shock Protein 10 and Brazzein Protein The optimized gene encoding the fusion protein comprising heat shock protein 10 and brazzein protein, recombinant expression vector, and transformed recombinant microorganism of the present invention are produced according to the following methods.

By using as a template a gene encoding the fusion protein comprising heat shock protein 10 and brazzein protein, which is used as a partner protein, fragments of the gene (SEQ ID NO: 1 or SEQ ID NO: 3) encoding a fusion protein which consists of 157 amino acids and comprises heat shock protein 10 and brazzein protein, in which the gene has been optimized such that it can be expressed in a host microorganism, was synthetically prepared.

To synthesize a gene encoding a fusion protein of brazzein protein-heat shock protein 10 (BRAZZEIN-HSP10; SEQ ID NO: 2) in which the brazzein protein is bound to the amino terminal (N-terminus) of the heat shock protein 10, E. coli-optimized 165 nucleotides encoding the brazzein protein were synthesized by using a forward primer (1) (5'-CATATGCAGGATAAATGT-3', SEQ ID NO: 5) and a reverse primer (1) (5'-ACCCGCCATGTATTCACA-3', SEQ ID NO: 6), and also, by using a forward primer (2) (5'-TGTGAATACATGGCGGGT-3', SEQ ID NO: 7) and a reverse primer (2) (5'-CTCGAGGTCAACGTATTT-3', SEQ ID NO: 8), E. coli-optimized 306 nucleotides encoding the heat shock protein 10 were synthesized. By using as a template each gene encoding the brazzein protein or heat shock protein 10, which has been synthesized according to the above method, and also the aforementioned forward primer (1) and reverse primer (2), a gene (SEQ ID NO: 1) consisting of 471 nucleotides encoding the fusion protein, in which the brazzein protein is bound to the N-terminus of the heat shock protein 10, was finally synthesized by a polymerase chain reaction (PCR).

To synthesize a gene encoding a fusion protein of heat shock protein 10-brazzein protein (HSP10-BRAZZEIN; SEQ ID NO: 4) in which the brazzein protein is bound to the carboxy terminal (C-terminus) of the heat shock protein 10, a gene consisting of 471 nucleotides (SEQ ID NO: 3) which encodes a fusion protein in which the brazzein protein is bound to the C-terminus of the heat shock protein 10 was synthesized in the same manner as described above by using a forward primer (3) (5'-CATATGGCGGGTCAGGCG-3', SEQ ID NO: 9) and a reverse primer (3) (5'-ATCCTG-CATGTCAACGTA-3', SEQ ID NO: 10), and also a forward primer (4) (5'-TACGTTGACATGCAGGAT-3', SEQ ID NO: 11) and a reverse primer (4) (5'-CTCGAGGTATT-CACAGTA-3', SEQ ID NO: 12)

According to digestion of the above gene fragment and recombinant plasmid with the same restriction enzymes (5' terminus NdeI and 3' terminus XhoI) followed by insertion, the recombinant plasmid (pET22b::H10BRAZZEIN and pET22b::BRAZZEINH10) shown in FIG. 1 was prepared. By transforming E. coli TOP10 with the prepared recombinant plasmid, the gene construct was obtained in large amount from the host organism.

After that, E. coli Rosetta2 (DE3) pLysS (Novagen, Germany) was transformed with the prepared recombinant plasmid so that a recombinant microorganism for producing the fusion protein comprising heat shock protein 10 and brazzein protein was prepared.

Example 2. Expression Induction, Separation, and Purification of Fusion Protein Comprising Heat Shock Protein 10 and Brazzein Protein E. coli Rosetta2 (DE3) pLysS prepared in Example 1 was cultured by using 1 ℓ LB medium (10% tryptophan, 10% sodium chloride, and 5% yeast extract) or BSS medium (1% tryptophan, 0.5% yeast extract, 1% glucose, and 0.1% HEPES (pH 7.0), Nexgen Biotechnologies, Inc.) till to have $OD_{600}$=0.6 to 0.8 for batch culture, or $OD_{600}$=15 to 20 for continuous culture which uses a 20 ℓ fermenter. After that, by adding 1 to 5 mM IPTG or 2% lactose (each at final concentration) to the cell culture medium, gene expression of the recombinant E. coli was induced. After inducing the gene expression, the cells were additionally cultured for 3 to 4 hours, and then collected by centrifuge. The resulting cells were completely suspended in phosphate buffered saline (8 g sodium chloride, 0.2 g potassium chloride, 1.44 g sodium hydrogen phosphate ($Na_2HPO_4$), and 0.24 g potassium dihydrogen phosphate ($KH_2PO_4$)/ ℓ , pH 7.4), and then disrupted by using an ultrasonic homogenizer so as to separate a solution containing the intracellular proteins. By using thus-separated solutions as a sample, protein expression was determined by 15% SDS-polyacrylamide gel electrophoresis. As a result, it was found that the fusion protein comprising heat shock protein 10 and brazzein protein is expressed in a crude lysate of cells which have been induced to undergo the expression by IPTG or lactose.

In order to separate and purify the fusion protein comprising heat shock protein 10 and brazzein protein of which expression has been confirmed, the inclusion body was solubilized with a solubilizing buffer solution (5 M urea, pH 11), and then subjected to a refolding process by ultrafine filtration (0.45 μm fine filtration membrane and 1 K ultrafine filtration membrane). By using a buffer solution for storage (PBS), the fusion protein comprising heat shock protein 10 and brazzein protein was finally separated.

Figure 2:
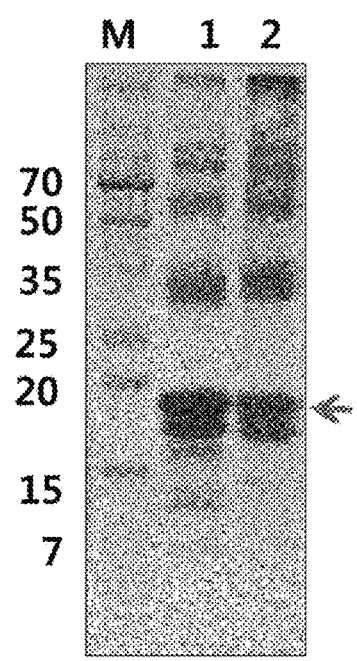
FIG. 2 is a photographic image of the SDS-PAGE gel of a fusion protein which has been finally separated and purified after expression of the fusion protein of the present invention in E. coli, in which M represents a size marker; 1 represents a fusion protein comprising brazzein protein and heat shock protein 10 (BRAZZEIN-HSP10); and 2 represents a fusion protein comprising heat shock protein 10 and brazzein protein (HSP10-BRAZZEIN).

For having complete purification of the above fusion protein, the separated fusion protein was passed through a nickel-agarose column at a rate of 1 to 3 ml/minute. Subsequently, the column was washed several times with a binding buffer solution, and an imidazole solution (pH 7.4) at a concentration of 50, 100, or 250 mM was applied to the column to fractionate and elute the fusion protein comprising heat shock protein 10 and brazzein protein, in which each fraction is eluted in an amount of 1 ml. Then, the imidazole in the buffer was removed by using 10 mM potassium phosphate solution so that the fusion protein was finally purified in pure state. To examine the result, 15% SDS-polyacrylamide gel electrophoresis was carried out. As a result, the finally purified fusion protein was found near the region having the expected size (about 17 to 20 kDa including His tag) (FIG. 2).

Example 3. Activity Measurement of Fusion Protein Comprising Heat Shock Protein 10 and Brazzein Protein: Dermal Fibroblast Cell Proliferation Effect After selecting the samples from which the presence of the fusion protein comprising heat shock protein 10 and brazzein protein has been confirmed as the protein is separated and purified in Example 2, activity of the fusion protein was measured.

Dermal fibroblast cells (Human Dermal Fibroblasts adult, HDFa cell) were cultured, and then treated with heat shock protein 10 (HSP10) or brazzein protein (BRAZZEIN) which have been used for the preparation of a fusion protein, or with the fusion protein comprising heat shock protein 10 and brazzein protein (BRAZZEIN-HSP10, HSP10-BRAZZEIN), each at a concentration of 0, 0.02, 0.2, 2.0, or 20 ppm, followed by culture for 3 days at 37° C. After that, proliferation of the dermal fibroblast cells was examined by crystal violet staining.

Figure 3:
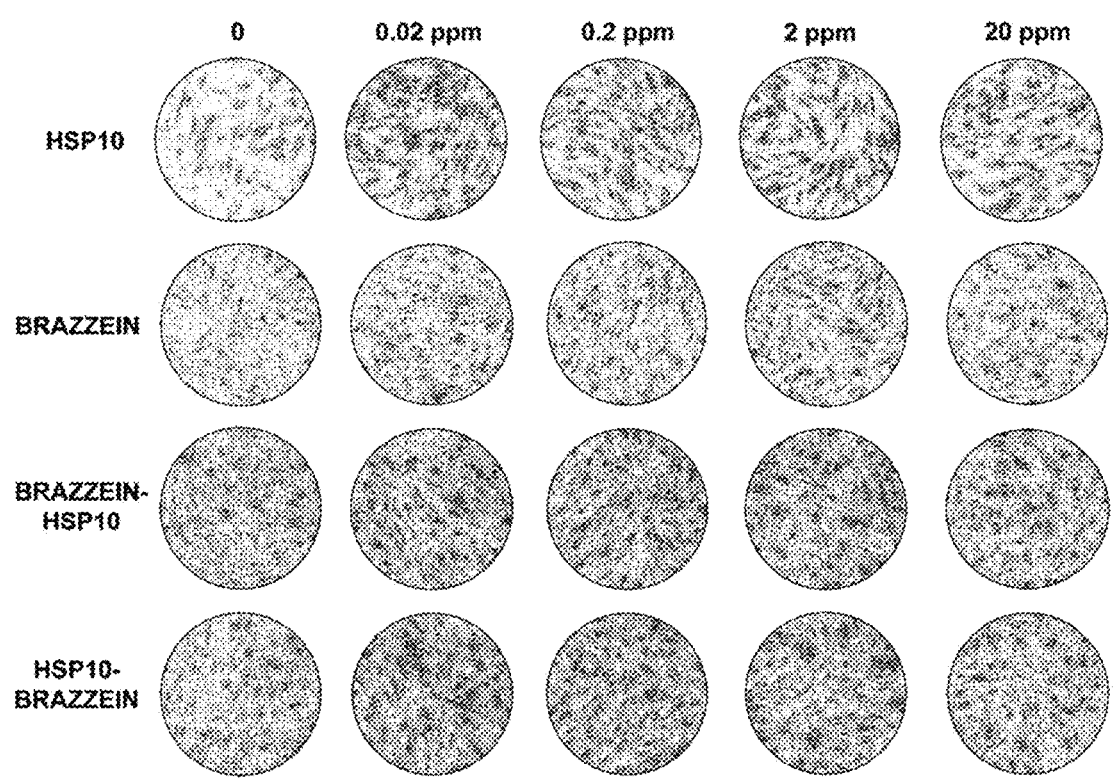
FIG. 3 shows the result of determining the cell proliferation of dermal fibroblast cells after treating the cells with heat shock protein 10 or brazzein protein (HSP10 and BRAZZEIN) that are used for the production of a fusion protein, or a fusion protein comprising brazzein protein and heat shock protein 10 (BRAZZEIN-HSP10 and HSP10-BRAZZEIN), in which the determination was made based on crystal violet staining after the treatment.

As a result, it was found that a more excellent dermal fibroblast proliferation effect is obtained as the concentration of the fusion protein comprising heat shock protein 10 and brazzein protein increases (FIG. 3). It was also observed that, compared to the group treated with a single protein (i.e., HSP10 or BRAZZEIN), the fusion protein comprising heat shock protein 10 and brazzein protein (BRAZZEIN-HSP10, HSP10-BRAZZEIN) exhibits a higher cell proliferation effect. Because the number of amino acids is 157 for the fusion protein while the number of amino acid is 103 or 54 for a single protein, i.e., heat shock protein 10 and brazzein protein, respectively, the mole number of the fusion protein is about ⅓ to ⅔ of the single protein when the treatment is carried out with a single protein or the fusion protein, which are present at the same concentration (for example, 0.02 ppm). Accordingly, it is recognized that, if there is a similar dermal fibroblast proliferation effect at the same concentration, the fusion protein has a dermal fibroblast proliferation effect that is 1.5 to 3 times higher than the single protein. As it can be realized from FIG. 3, compared to the treatment with a single protein, the dermal fibroblast proliferation effect is higher when the treatment is carried out with the fusion protein comprising heat shock protein 10 and brazzein protein, and thus the fusion protein is found to have a dermal fibroblast proliferation effect that is at least 1.5 to 3 times higher than the single protein. Based on this result, it is recognized that the fusion protein comprising heat shock protein 10 and brazzein protein has an excellent dermal cell proliferation effect.

Example 4. Activity Measurement of Fusion Protein Comprising Heat Shock Protein 10 and Brazzein Protein: Anti-Oxidation Effect In order to examine the anti-oxidation effect of the fusion protein comprising heat shock protein 10 and brazzein protein, DPPH (1,1-diphenyl-2-pycryl-hydrazyl) method, which is one of the methods for measuring the free radical scavenging activity, was used.

Figure 4:
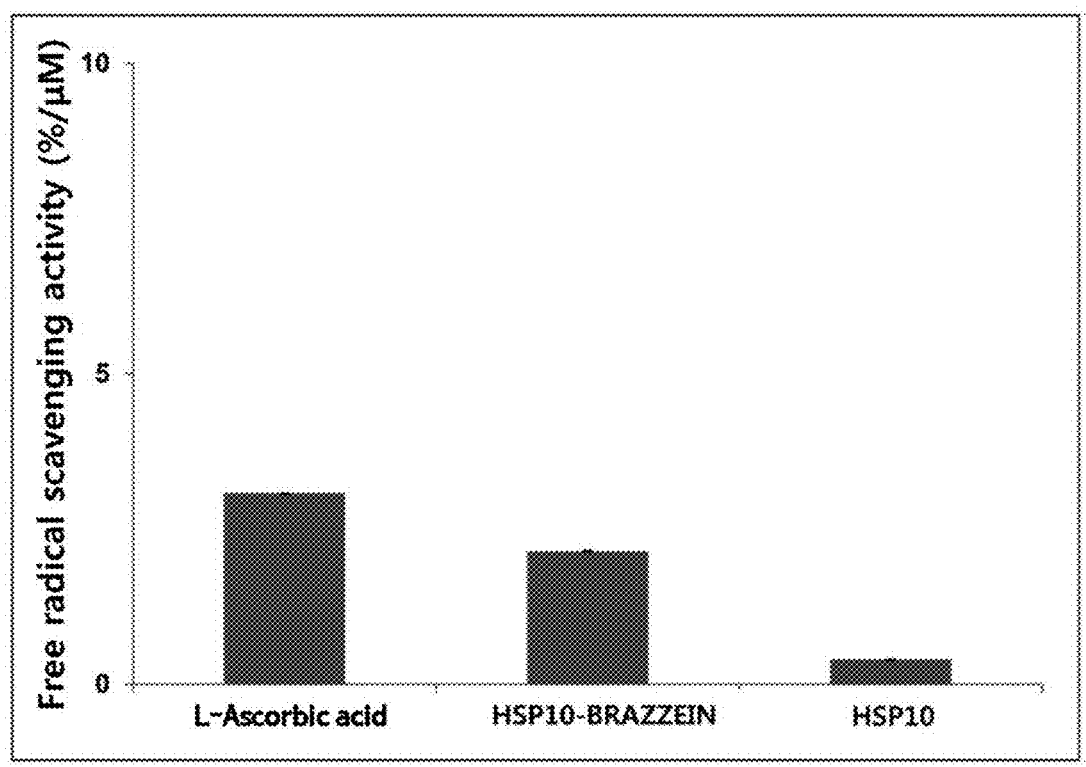
FIG. 4 shows the result of determining the anti-oxidation effect of the fusion protein comprising heat shock protein 10 and brazzein protein.

In order to examine the anti-oxidation activity of the fusion protein comprising heat shock protein 10 and brazzein protein, L-ascorbic acid was used as a control group. For the test, heat shock protein 10, a fusion protein comprising heat shock protein 10 and brazzein protein, and L-ascorbic acid were prepared each at 1 μM concentration while DPPH was prepared at concentration of 0.2 mM. After mixing each of them at a ratio of 1:1, they were allowed to stand for 30 minutes at 37° C. After that, the absorbance at 520 nm was measured by using an ELISA reader. The free radical scavenging activity (%) was calculated based on the following equation 1, and the results are shown in FIG. 4.

Free radical scavenging activity (%)=100−(($B/A$)*100) [Equation 1]

A: Absorbance by control group which has not been treated with any test sample

B: Absorbance by test group which has been treated with test sample

As a result, it was shown that the fusion protein comprising heat shock protein 10 and brazzein protein showed lower free radical scavenging activity than L-ascorbic acid as a positive control group. However, it showed the free radical scavenging activity that has increased by about 5 times or more compared to the group which has been treated with heat shock protein 10 only. Namely, as the fusion protein comprising heat shock protein 10 and brazzein protein of the present invention was found to have a very high anti-oxidation activity, it is believed to have a skin aging preventing effect.

The invention claimed is:

1. A fusion protein consisting of the amino acid sequence of SEQ ID NO: 2 or SEQ ID NO: 4.

2. A gene encoding the fusion protein of claim 1.

3. The gene according to claim 2, wherein the gene consists of the nucleotide sequence of SEQ ID NO: 1 or SEQ ID NO: 3.

4. A recombinant vector comprising the gene of claim 3.

5. A host cell transformed with the recombinant vector of claim 4.

6. A method for producing a fusion protein consisting of the amino acid sequence of SEQ ID NO: 2 or 4 in a host cell, wherein the method comprises transforming the host cell with the recombinant vector of claim 4 to overexpress the gene encoding the fusion protein.

7. The method of claim 6, wherein the host cell is Escherichia coli (E. coli).

8. A cosmetic composition for skin regeneration and wrinkle amelioration, comprising, as an effective component, a fusion protein consisting of the amino acid sequence of SEQ ID NO: 2 or SEQ ID NO: 4.

9. A recombinant vector comprising the gene of claim 2.

10. A host cell transformed with the recombinant vector of claim 9.

11. A method for producing a fusion protein consisting of the amino acid sequence of SEQ ID NO: 2 or 4 in a host cell, wherein the method comprises transforming the host cell with the recombinant vector of claim 9 to overexpress the gene encoding the fusion protein.

12. The method of claim 11, wherein the host cell is E. coli.

13. A method for skin regeneration and wrinkle amelioration in a subject, wherein the method comprises applying to the skin of the subject a composition comprising the fusion protein of claim 1.

\* \* \* \* \*

SEQUENCE LISTING

```
<160> NUMBER OF SEQ ID NOS: 12

<210> SEQ ID NO 1
<211> LENGTH: 471
<212> TYPE: DNA
<213> ORGANISM: Artificial Sequence
<220> FEATURE:
<223> OTHER INFORMATION: Brazzein-HSP10 fusion protein

<400> SEQUENCE: 1
atgcaggata aatgtaaaaa agtttatgaa aactacccgg ttagtaaatg ccagttagct         60
```

```
aaccagtgta actatgactg caaactggac aaacacgcgc gcagcggcga gtgcttctat    120
gatgaaaaac gtaacctgca atgtatctgt gattactgtg aatacatggc gggtcaggcg    180
ttccgtaaat tcctgccgct gttcgaccgt gttctggttg aacgttctgc ggcggaaacc    240
gttaccaaag gtggtatcat gctgccggaa aaatctcagg gtaaagttct gcaggcgacc    300
gttgttgcgg ttggttctgg ttctaaaggt aaaggtggtg aaatccagcc ggtttctgtt    360
aaagttggtg acaaagttct gctgccggaa tacggtggta ccaaagttgt tctggacgac    420
aaagactact tcctgttccg tgacggtgac atcctgggta aatacgttga c             471
```

<210> SEQ ID NO 2
<211> LENGTH: 157
<212> TYPE: PRT
<213> ORGANISM: Artificial Sequence
<220> FEATURE:
<223> OTHER INFORMATION: Brazzein-HSP10 fusion protein

<400> SEQUENCE: 2

```
Met Gln Asp Lys Cys Lys Lys Val Tyr Glu Asn Tyr Pro Val Ser Lys
1               5                   10                  15

Cys Gln Leu Ala Asn Gln Cys Asn Tyr Asp Cys Lys Leu Asp Lys His
                20                  25                  30

Ala Arg Ser Gly Glu Cys Phe Tyr Asp Glu Lys Arg Asn Leu Gln Cys
            35                  40                  45

Ile Cys Asp Tyr Cys Glu Tyr Met Ala Gly Gln Ala Phe Arg Lys Phe
        50                  55                  60

Leu Pro Leu Phe Asp Arg Val Leu Val Glu Arg Ser Ala Ala Glu Thr
65                  70                  75                  80

Val Thr Lys Gly Gly Ile Met Leu Pro Glu Lys Ser Gln Gly Lys Val
                85                  90                  95

Leu Gln Ala Thr Val Val Ala Val Gly Ser Gly Ser Lys Gly Lys Gly
            100                 105                 110

Gly Glu Ile Gln Pro Val Ser Val Lys Val Gly Asp Lys Val Leu Leu
        115                 120                 125

Pro Glu Tyr Gly Gly Thr Lys Val Val Leu Asp Asp Lys Asp Tyr Phe
    130                 135                 140

Leu Phe Arg Asp Gly Asp Ile Leu Gly Lys Tyr Val Asp
145                 150                 155
```

<210> SEQ ID NO 3
<211> LENGTH: 471
<212> TYPE: DNA
<213> ORGANISM: Artificial Sequence
<220> FEATURE:
<223> OTHER INFORMATION: HSP10-Brazzein fusion protein

<400> SEQUENCE: 3

```
atggcgggtc aggcgttccg taaattcctg ccgctgttcg accgtgttct ggttgaacgt     60
tctgcggcgg aaaccgttac caaaggtggt atcatgctgc cggaaaaatc tcagggtaaa    120
gttctgcagg cgaccgttgt tgcggttggt tctggttcta aaggtaaagg tggtgaaatc    180
cagccggttt ctgttaaagt tggtgacaaa gttctgctgc cggaatacgg tggtaccaaa    240
gttgttctgg acgacaaaga ctacttcctg ttccgtgacg gtgacatcct gggtaaatac    300
gttgacatgc aggataaatg taaaaaagtt tatgaaaact acccggttag taaatgccag    360
ttagctaacc agtgtaacta tgactgcaaa ctggacaaac gcgcgcag cggcgagtgc      420 ttctatgatg aaaaacgtaa cctgcaatgt atctgtgatt actgtgaata c              471
```

```
<210> SEQ ID NO 4
<211> LENGTH: 157
<212> TYPE: PRT
<213> ORGANISM: Artificial Sequence
<220> FEATURE:
<223> OTHER INFORMATION: HSP10-Brazzein fusion protein

<400> SEQUENCE: 4

Met Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp Met Gln Asp Lys Cys Lys Lys Val Tyr Glu
            100                 105                 110

Asn Tyr Pro Val Ser Lys Cys Gln Leu Ala Asn Gln Cys Asn Tyr Asp
        115                 120                 125

Cys Lys Leu Asp Lys His Ala Arg Ser Gly Glu Cys Phe Tyr Asp Glu
    130                 135                 140

Lys Arg Asn Leu Gln Cys Ile Cys Asp Tyr Cys Glu Tyr
145                 150                 155

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
catatgcagg ataaatgt                                                       18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
acccgccatg tattcaca                                                       18

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
tgtgaataca tggcgggt                                                       18

<210> SEQ ID NO 8
```

```
<211> LENGTH: 18
<212> TYPE: DNA
<213> ORGANISM: Artificial Sequence
<220> FEATURE:
<223> OTHER INFORMATION: primer

<400> SEQUENCE: 8
ctcgaggtca acgtattt                                              18

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
catatggcgg gtcaggcg                                              18

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
atcctgcatg tcaacgta                                              18

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
tacgttgaca tgcaggat                                              18

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
ctcgaggtat tcacagta                                              18
```